(12) United States Patent
Skorobogatiy et al.

(10) Patent No.: US 7,460,238 B2
(45) Date of Patent: Dec. 2, 2008

(54) PLASMON EXCITATION BY THE GAUSSIAN-LIKE CORE MODE OF A PHOTONIC CRYSTAL WAVEGUIDE

(75) Inventors: Maksim Skorobogatiy, Kirkland (CA); Andrei V. Kabashin, Montréal (CA)

(73) Assignee: Corporation De L'ecole Polytechnique De Montreal, Montreal, Quebec (CA)

(*) Notice: Subject to any disclaimer, the term of this patent is extended or adjusted under 35 U.S.C. 154(b) by 41 days.

(21) Appl. No.: 11/739,270

(22) Filed: Apr. 24, 2007

(65) Prior Publication Data
US 2008/0266567 A1    Oct. 30, 2008

(51) Int. Cl.
*G01N 21/55* (2006.01)
*H01S 3/14* (2006.01)
*H01S 3/08* (2006.01)
*G02B 6/12* (2006.01)
*G02B 6/02* (2006.01)

(52) U.S. Cl. .................... 356/447; 356/445; 356/448; 372/39; 372/96; 385/14; 385/123

(58) Field of Classification Search ............ 257/79–98; 356/445–448; 372/39–51, 96–99; 385/14–35
See application file for complete search history.

(56) References Cited

U.S. PATENT DOCUMENTS 6,180,415 B1 *   1/2001  Schultz et al. ............ 436/518
7,015,471 B2 *   3/2006  Franzen et al. ........... 250/338.1
7,148,516 B2 *  12/2006  Gruhlke .................... 257/89

OTHER PUBLICATIONS

Ctyroky et al., "Theory and Modelling of Optical Waveguide Sensors Utilising Surface Plasmon Resonance,", Sensors and Actuators B 54, Elsevier Science S. A.,1999, pp. 66-73.

(Continued)

*Primary Examiner*—L. G. Lauchman
*Assistant Examiner*—Jarreas C Underwood
(74) *Attorney, Agent, or Firm*—Fay Kaplun & Marcin, LLP

(57) ABSTRACT

A sensor and method for surface plasmon resonance sensing, wherein a small variation of the refractive index of an ambient medium results in a large variation of loss of a sensing mode. The surface plasmon resonance sensor comprises an antiguiding waveguide including a core characterized by a refractive index and a reflector surrounding the core. The reflector has an external surface and is characterized by a band gap and a refractive index higher than the refractive index of the core. A coating is deposited on the external surface of the core, the coating defining with the ambient medium a coating/ambient medium interface. In operation, the coating is in contact with the ambient medium, and the antiguiding waveguide is supplied with an electromagnetic radiation to (a) propagate a mode for sensing having an effective refractive index lower than the refractive index of the core and higher than a refractive index of an ambient medium and (b) produce surface plasmons at the coating/ambient medium interface. The mode for sensing is phase-matched with the surface plasmons at a wavelength within the band gap and a variation of the refractive index of the ambient medium results in a variation of loss of the sensing mode to detect a characteristic of the ambient medium.

26 Claims, 11 Drawing Sheets

OTHER PUBLICATIONS

Dostalek et al., "Surface Plasmon Resonance Biosensor Based on Integrated Optical Waveguide," Sensors and Actuators B 76, Elsevier Science S. A., 2001, pp. 8-12.

Grigorenko et al., "Phase Jumps and Interferometric Surface Plasmon Resonance Imaging,", Applied Physics Letters, American Institute of Physics, vol. 75, No. 25, Dec. 20, 1999, pp. 3917-3919.

Gupta et al., "Sensitivity Evaluation of a Multi-Layered Surface Plasmon Resonance-based Fiber Optic Sensor: a Theoretical Study," Sensors and Actuators B 107, Elsevier Science S. A., 2005, pp. 40-46.

Harris et al., "Waveguide Surface Plasmon Resonance Sensors," Sensors and Actuators B 29, Elsevier Science S. A., 1995, pp. 261-267.

Homola et al., "A Surface Plasmon Resonance Based Integrated Optical Sensors," Sensors and Actuators B38-39, Elsevier Science S. A., 1997, pp. 286-290.

Johnson et al., "Low-loss Asymptotically Single-Mode Propagation in Large-core OmniGuide Fibers," Optics Express, Vo,. 19, No. 13, Dec. 17, 2001, pp. 748-779.

Kabashin et al., "Surface Plasmon Resonance Interferometer for Bio- and Chemical-Sensors," Optics Communications 150, Elsevier Science S. A., 1998, pp. 5-8.

Karalis et al., "Surface-Plasmon-Assisted Guiding of Broadband Slow and Subwavelength Light in Air," Physical Review Letters, PRL 95, The American Physical Society, Aug. 2005, pp. 063901-1-0639014.

Melendez et al., "A Commercial Solution for Surface Plasmon Sensing," Sensors and Actuators B 35-36, Elsevier Science S. A., 1996, pp. 212-216.

Sheridan et al., "Phase Interrogation of an Integrated Optical SPR Sensor," Sensors and Actuators B 97, Elsevier Science S. A., 2004, pp. 114-121.

Shin et al., "All-Angle Negative Refraction for Surface Plasmon Waves Using a Metal-Dielectric-Metal Structure," Physical Review Letters, PRL 96, The American Physical Society, Feb. 24, 2006, pp. 073907-1-073907-4.

Shin et al., "Omnidirectional Resonance in a Metal-Dielectric-Metal Geometry," Applied Physics Letters, American Institute of Physics, vol. 84, No. 22, May 31, 2004, pp. 4421-4423.

Skorobogatiy, "Transverse Light Guides in Microstructured Optical Fibers," Optics Letter, Optical Society of America, vol. 31, No. 3, Feb. 1, 2006, pp. 314-316.

Weiss et al., "Experimental Investigation of a Surface Plasmon-Based Integrated-Optic Humidity Sensor," Electronic Letters, vol. 32, No. 9, Apr. 1996, pp. 842-843.

Weisser et al., "Refractive Index and Thickness Determination of Monolayers by Multi Mode Waveguide Coupled Surface Plasmons," Sensors and Actuators B 56, Elsevier Science S. A., 1999, pp. 189-197.

Zhang et al., "Optical Chemical Sensing Employing Surface Plasmon Resonance," Electronics Letters, vol. 24, No. 23, Nov. 1988, pp. 1469-1470.

\* cited by examiner

PLASMON EXCITATION BY THE GAUSSIAN-LIKE CORE MODE OF A PHOTONIC CRYSTAL WAVEGUIDE

FIELD OF THE INVENTION

The present invention generally relates to a surface plasmon resonance (SPR) sensor. More specifically, but not exclusively, the present invention is concerned with an antiguiding waveguide-based SPR sensor, for example a photonic crystal waveguide-based SPR sensor wherein small variations of an ambient refractive index external to the SPR sensor result in large variations of losses in one mode of the antiguiding waveguide. The antiguiding waveguide-based SPR sensor can be advantageously used for sensing analytes present in an ambient medium since the refractive index of the ambient medium will vary as a result of the presence of the analytes.

BACKGROUND OF THE INVENTION

SPR is an oscillation of a plasma of free electrons which exists, generally but not exclusively, at a metal surface boundary. SPR results in a resonant transfer of energy from photons, incident to the metal surface, to the plasma at the metal surface boundary. The quasiparticle resulting from the quantization of such an oscillation is a plasmon.

Typically, a SPR sensor comprises a prism and a metal film atop thereof. The surface of the metal film opposite to the prism forms an interface with an ambient medium. Typically, the metal film is made of gold or silver. An electromagnetic radiation beam, such as p-polarized light, is propagated through the prism and is totally internally reflected on the metal film, as a result of the metal film's having a refractive index lower than that of the prism. When some photons of the electromagnetic radiation beam incident to the prism-metal film interface resonantly transfer their energy to the electron plasma at the metal film-ambient medium interface, SPR occurs.

Such a transfer of energy is made possible through an evanescent wave partially penetrating into the metal. The evanescent wave is produced by the electromagnetic radiation propagating through the prism and incident to the metal film. In this manner, the electromagnetic radiation looses part of its energy to the evanescent wave and thus produces a coupling between a mode of the electromagnetic radiation and a mode of the surface plasmons.

SPR can be detected through a dip in an angular dependence of the intensity of the reflected electromagnetic radiation beam, or through a dip in a spectral intensity of the reflected electromagnetic radiation beam. In turn, position of the dip depends on the refractive index of the ambient medium. As a result, a change of the refractive index of the ambient medium will produce a shift of the dip.

After a SPR sensor has been calibrated for the ambient medium, it can be used to detect bio-molecules and other bio-materials, which tend to attach to some metal films such as gold and silver films. Upon attachment to the metal film, the bio-molecules or other bio-materials will produce a shift of the dip, thus enabling their being detected.

Propagating at the metal/dielectric interface, surface plasmons [1] are extremely sensitive to changes in the refractive index of the dielectric. This feature constitutes the core of many Surface Plasmon Resonance (SPR) sensors. Typically, SPR sensors are implemented in a Kretschmann-Raether prism geometry to propagate p-polarized light through a glass prism and reflect it from a thin metal film made, for example, of gold or silver and deposited on a facet of the prism [2]. The presence of a prism allows phase matching of an incident electromagnetic wave with a plasmonic wave at the metal/ambient dielectric interface at a specific combination of the angle of incidence and wavelength. Mathematically, phase matching condition is expressed as an equality between a plasmon wavevector and a projection of a wavevector of the incident electromagnetic wave along the metal/ambient dielectric interface. Since plasmon excitation condition depends resonantly on the value of the refractive index of the ambient medium within 200-300 nm from the metal/ambient dielectric interface, this method enables, for example, detection with unprecedented sensitivity of biological binding events on the metal surface [3]. The course of a biological reaction can then be followed by monitoring angular [3,4], spectral [5] and/or phase [6, 7] characteristics of the reflected light. However, the high cost and large size of commercially available systems [8] makes them useful only in laboratories, while many important fields and other applications remain out of the applicability of the method.

In order to miniaturize SPR biosensors, several waveguide-based implementations have been developed [9, 10, 11, 12, 13, 14, 15, 16, 17, 18, 19]. In these sensors, light is launched into a waveguide core and then coupling of a guided mode with a plasmonic mode is used to probe for the changes in the ambient environment. To excite efficiently a surface plasmon the phase matching condition between the plasmon and waveguide modes has to be satisfied, which mathematically amounts to equality between their modal propagation constants. Ideally, one would use a single mode waveguide (SMW) with all the power traveling in a single Gaussian-like core mode operating near the point of resonant excitation of a plasmon (FIG. 1a). Near such a point most of the energy launched into the waveguide core could be efficiently transferred into a plasmon mode. Such an approach based on planar waveguides has been indeed demonstrated in the visible spectral region to provide several compact designs of SPR biosensors [9, 10, 11, 12, 13, 14]. However, for such single-mode, low index-contrast waveguides, the SPR coupling is realized at essentially grazing angles of modal incidence on the metal layer. As follows from the basic SPR theory [1], coupling at such grazing incidence angles leads to an inevitable decrease of sensitivity of a SPR sensor. Moreover, due to limitation to the lowest attainable value of the refractive index of waveguide materials, such sensors were demonstrated mostly in the visible spectral region where phase matching condition is easiest to reach. In principle, to increase the angle of modal incidence on the metal layer, high index contrast waveguides could be employed. However, as shown in FIG. 1a, quick inspection of a corresponding band diagram shows that phase matching between plasmon mode and a fundamental waveguide mode is not easy to realize. This is due to the fact that an effective refractive index of such a mode is close to the refractive index of the material forming the core of the waveguide, which is typically larger than 1.45 due to material limitations. The refractive index of a plasmon is close to the refractive index n of the ambient medium which is typically air, wherein n=1, and water, wherein n=1.3. Thus, large discrepancy in the refractive indices makes it hard to achieve phase matching between the two modes, with an exception with higher frequencies ($\lambda$<650 nm) where the plasmon dispersion relation deviates substantially from that of an analyte material.

Another solution to the phase matching and incidence angle problem is a coupling to a plasmon via the high order modes of a multimoded waveguide [15, 16, 17, 18, 19] (MMW). As can be seen from the plot of their dispersion relations (FIG. 1b), such modes can have significantly lower effective refractive indices than a waveguide core index. In such a set-up light has to be launched into the waveguide as to excite high order modes some of which will be phase matched with a plasmon mode. As only a fraction of higher order modes are phase matched to a plasmon, then only a fraction of total launched power will be coupled to the plasmon.

SUMMARY OF THE INVENTION

According to the present invention, there is provided a surface plasmon resonance sensor for an ambient medium characterized by a refractive index, the surface plasmon resonance sensor comprising:

an antiguiding waveguide comprising: a core characterized by a refractive index; and a reflector surrounding the core, the reflector having an external surface and being characterized by a band gap and a refractive index higher than the refractive index of the core; and a coating deposited on the external surface of the core, the coating defining with the ambient medium a coating/ambient medium interface suitable to support surface plasmons;

wherein, in operation:

the coating is in contact with the ambient medium;

the antiguiding waveguide is supplied with an electromagnetic radiation to (a) propagate a mode for sensing having an effective refractive index lower than the refractive index of the core and higher than the refractive index of the ambient medium and (b) produce surface plasmons at the coating/ambient medium interface;

the mode for sensing is phase-matched with the surface plasmons at a wavelength within the band gap; and a variation of the refractive index of the ambient medium results in a variation of loss of the sensing mode to detect a feature of the ambient medium.

Also in accordance with the present invention, there is provided a method for surface plasmon resonance sensing a feature of an ambient medium characterized by a refractive index, comprising:

providing an antiguiding waveguide comprising: a core characterized by a refractive index; and a reflector surrounding the core, the reflector having an external surface and being characterized by a band gap and a refractive index higher than the refractive index of the core; and depositing a coating on the external surface of the core, the coating defining with the ambient medium a coating/ambient medium interface suitable to support surface plasmons;

bringing the coating in contact with the ambient medium;

supplying the antiguiding waveguide with an electromagnetic radiation to (a) propagate a mode for sensing having an effective refractive index lower than the refractive index of the core and higher than the refractive index of the ambient medium and (b) produce surface plasmons at the coating/ambient medium interface;

phase-matching the mode for sensing with the surface plasmons at a wavelength within the band gap; and sensing a variation of the refractive index of the ambient medium through a variation of loss of the sensing mode to detect a feature of the ambient medium.

The foregoing and other objects, advantages and features of the present invention will become more apparent upon reading of the following non-restrictive description of an illustrative embodiment thereof, given by way of example only, with reference to the accompanying drawings.

DETAILED DESCRIPTION

The non-restrictive illustrative embodiment of a photonic crystal waveguide-based SPR sensor and corresponding method according to the present invention will now be described.

In the non-restrictive illustrative embodiment of the present invention, SPR is produced by excitation with a lowest loss TM polarized Gaussian-like leaky core mode of a band gap guiding photonic crystal (PC) or, more generally, an antiguiding waveguide. The term Gaussian-like refers to a bell-shaped distribution of the leading energy flux component (component along the waveguide direction) in the core region of the waveguide. The terms band gap guiding and antiguiding both refer to a transmission mechanism wherein an effective refractive index $n_{eff}$ of a waveguide propagating mode is smaller than that of the waveguide immediate cladding. Such unusual modes are called leaky modes since, even in the absence of material losses, the propagation loss of such modes is non-zero due to slow radiation of energy from the core region, i.e. leaking, into the cladding. Moreover, in the case of band gap guiding outside a waveguide core, when this band gap guiding occurs at the wavelength in the band gap of a reflector surrounding the waveguide core, leaky modes exhibit an overall evanescent decay into such a reflector with modal radiation losses reducing with the size of the reflector. Examples of antiguiding systems are gas and water filled glass capillaries, hollow air filled core Bragg and microstructured fibers [24], and air core planar photonic crystal waveguides. As defined above the antiguiding mechanism is a broader guiding mechanism which includes, as a particular case, a band gap guiding mechanism. In the non-restrictive illustrative embodiment of the present invention, a band gap guiding design is used to integrate advantages of both single mode and multimode schemes, using a photonic crystal. It should be noted, however, that any antiguiding waveguide could be used. When a lowest loss mode of an antiguiding PC waveguide is used over sufficient SPR sensor length, such a waveguide can be considered as an effective single mode waveguide at any frequency within the band gap of the photonic crystal, due to efficient modal discrimination by radiation losses. This does not mean that device length always has to be such as to enable an effective single mode regime. Coupling from an external laser source into the lowest loss mode is very efficient as this mode can be made Gaussian-like, even for TM polarization [20]. Moreover, the dispersion relation and effective propagation angle of such an antiguided mode is easy to vary by changing the properties of a confining Photonic Band Gap reflector. This allows phase matching with plasmon at almost any desired wavelength for almost any analyte material.

Figure 4:
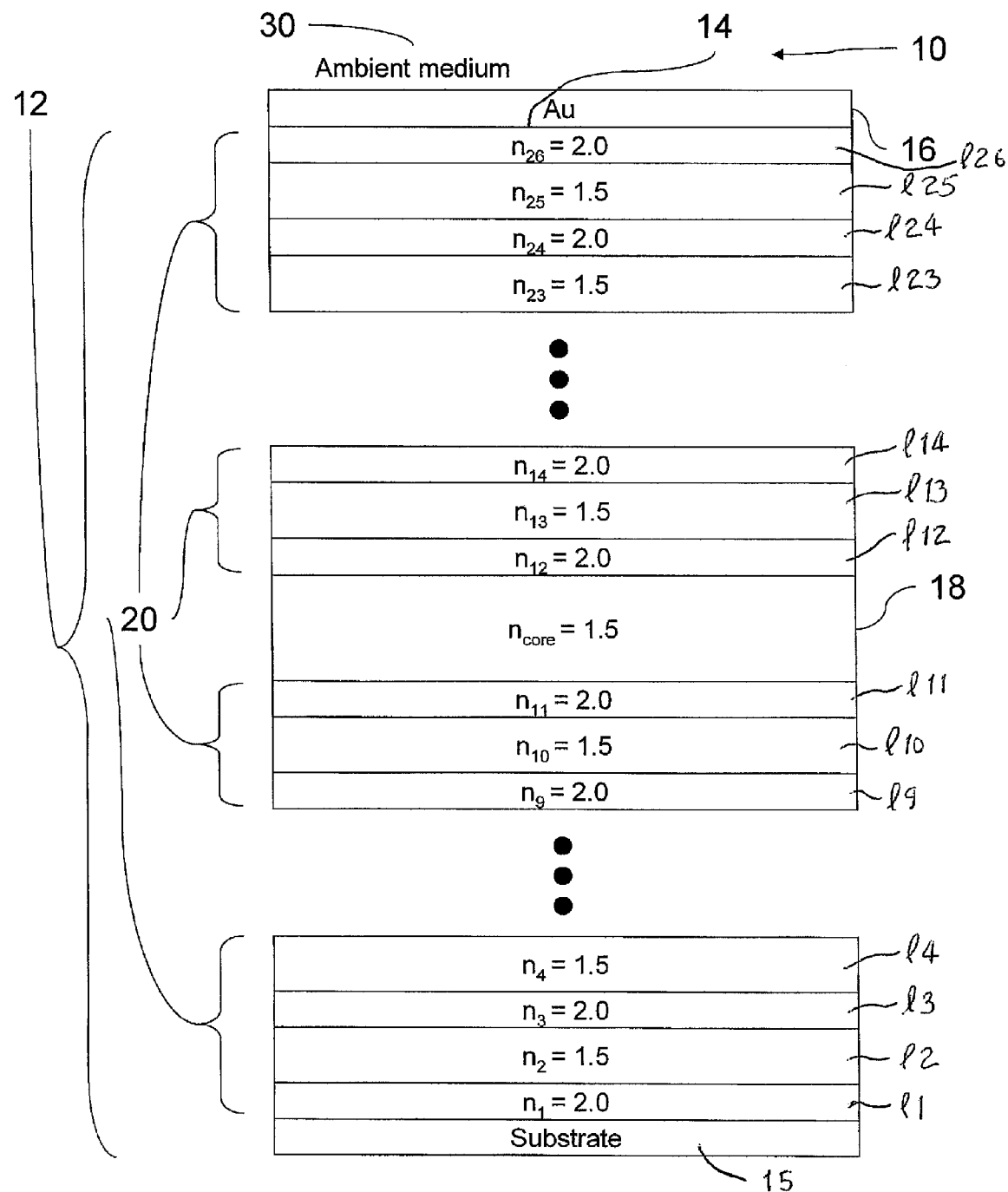
FIG. 4 is a schematic view of a non-restrictive illustrative embodiment of a photonic crystal waveguide-based SPR sensor according to the present invention.

Turning now to FIG. 4, the photonic crystal waveguide-based SPR sensor 10 according to the non-restrictive illustrative embodiment, comprises a photonic crystal 12, having a surface 14 on which a coating 16 is deposited. The composition of the coating 16 is chosen so as to: (i) support SPR using, for example, metallic or semiconductor material; and (ii) facilitate recognition of analyte molecules (not shown) thus constituting a sensing layer for inorganic and organic (bio-) molecules. In the present illustrative embodiment, the coating 16 is made of a film of gold 50 nm thick. The coating 16 can also be made of a film of any other metal capable of supporting plasmon excitation, for example silver, copper, nickel, titanium, tantalum, chromium or others.

Still referring to FIG. 4, the photonic crystal 12 comprises a core 18 surrounded by a multilayer reflector 20. The multilayer reflector 20 comprises, in the non-restrictive illustrative embodiment, a number of 26 individual layers I1-I26. Layers I1 to I11 are stacked in numerical order on one side of the core 18 opposite to the coating 16, with layer I11 applied to one side of the core 18. In the same manner, layer I12 to I26 are stacked in numerical order between the core 18 and the coating 16, with layer I12 applied to the core 18 and layer I26 applied to the coating 16. Therefore, the waveguide core 18 is interposed between the individual layers I11 and I12. Each individual layer I1, I2 . . . I26 is characterized by a respective refractive index, $n_{I1}$, $n_{I2}$, . . . and $n_{I26}$.

The SPR sensor 10 of FIG. 4 can be operated in an ambient medium 30 characterized by a refractive index $n_{analyte}$. Typically, the ambient medium 30 contains analytes (not shown), which has an effect on the refractive index thereof. In the non-restrictive illustrative embodiment:

The ambient medium 30, i.e. the analyte, is water with a refractive index $n_{analyte}=1.332$;
The refractive index of the core 18 is $n_{core}=1.5$;
The refractive indices of the successive individual layers I1-I26 alternate between 1.5 and 2.0, wherein the two individual layers I11 and I12 applied to the opposite sides of the waveguide core 18 having both a refractive index of 2.0.

Of course, the SPR sensor 10 can be provided with a substrate layer 15 on which the individual layer I1 is applied. The refractive index of the substrate layer 15, in principle, can take any value. In the non-restrictive illustrative embodiment of the present invention, the refractive index of the substrate layer 15 is 1.5. It is important to note that the refractive index of the substrate layer 15 can, in principle, have a value lower than that of a core guided mode. In this case, strictly speaking, the leaky band gap guided mode will be guided by the total internal reflection at the photonic crystal/substrate interface. In that case, however, the term leaky mode should be rather applied to the guidance in the waveguide core 18 versus guiding in a photonic crystal cladding (multilayer reflector 20) where, as it is the case in antiguiding waveguides, the main goal is to force light to propagate in the waveguide core surrounded by a higher refractive index photonic crystal cladding.

In the non-restrictive illustrative embodiment, plasmon excitation is achieved by a Gaussian-like TM polarized mode of photonic crystal 12 (FIG. 1c) in which light confinement in the lower refractive index core 18 is achieved by the surrounding multilayer reflector 20 (individual layers I1-I11 on one side and individual layers I12-I26 on the other, opposite side of the core 18).

Figure 1A:
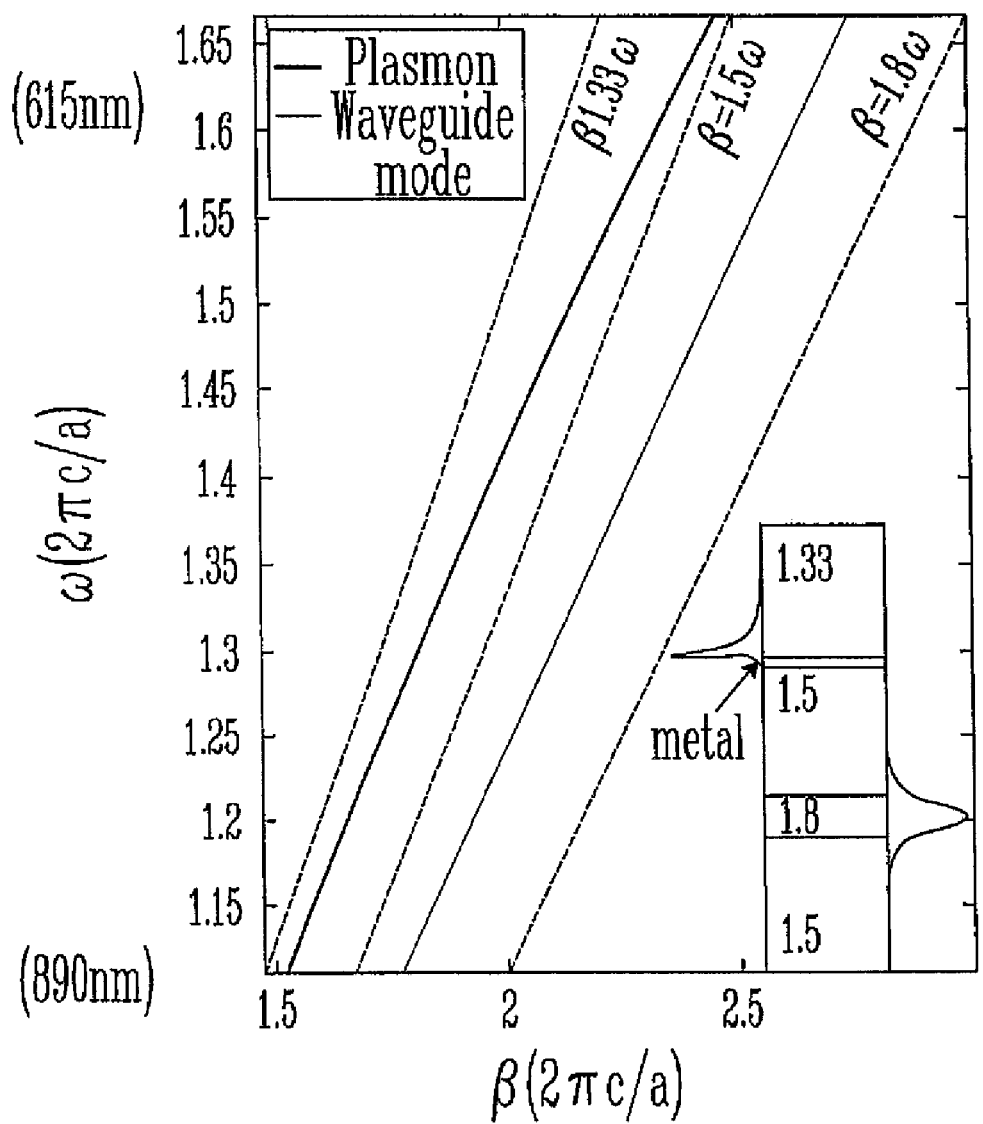
FIG. 1a represents band diagrams of a single mode waveguide (SMW) where all the power travels in a single Gaussian-like core mode operating near the point of resonant excitation of a Plasmon.
Figure 1B:
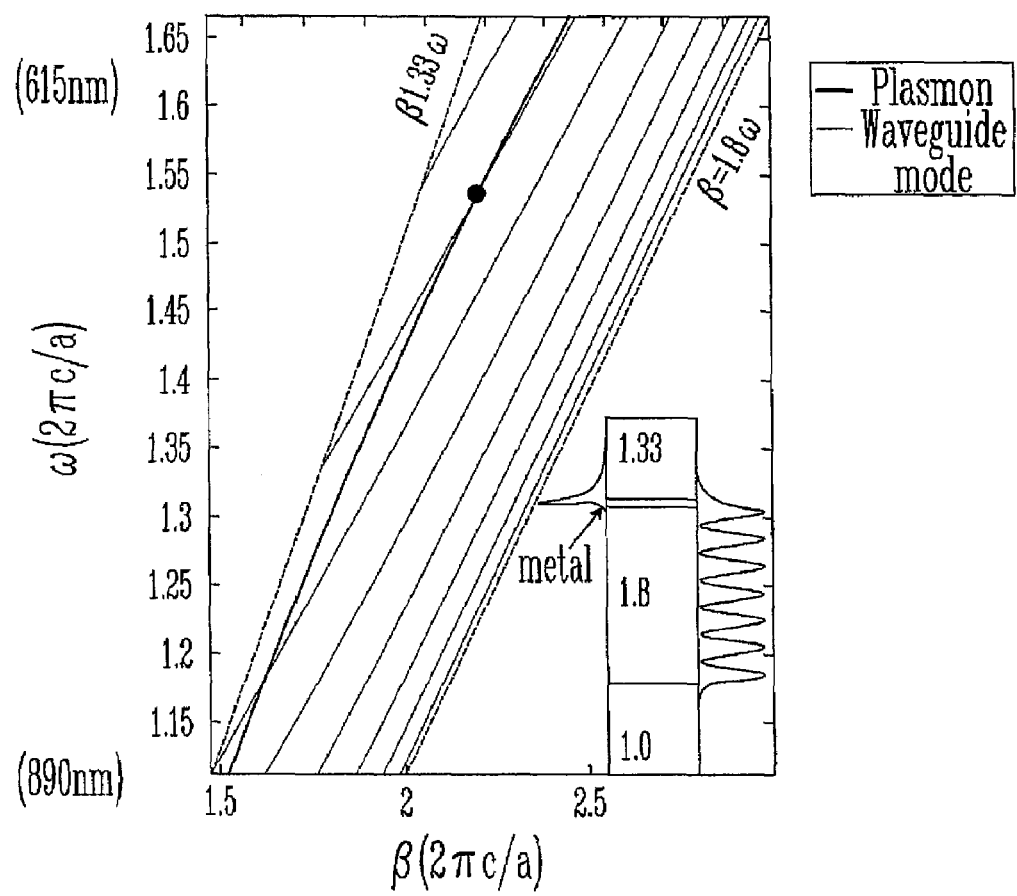
FIG. 1b represents band diagrams of high order modes of a multimoded waveguide (MMW), showing the dispersion of these modes with respect to a plasmon and showing that such modes can have significantly lower effective refractive indices than a waveguide core index.
Figure 1C:
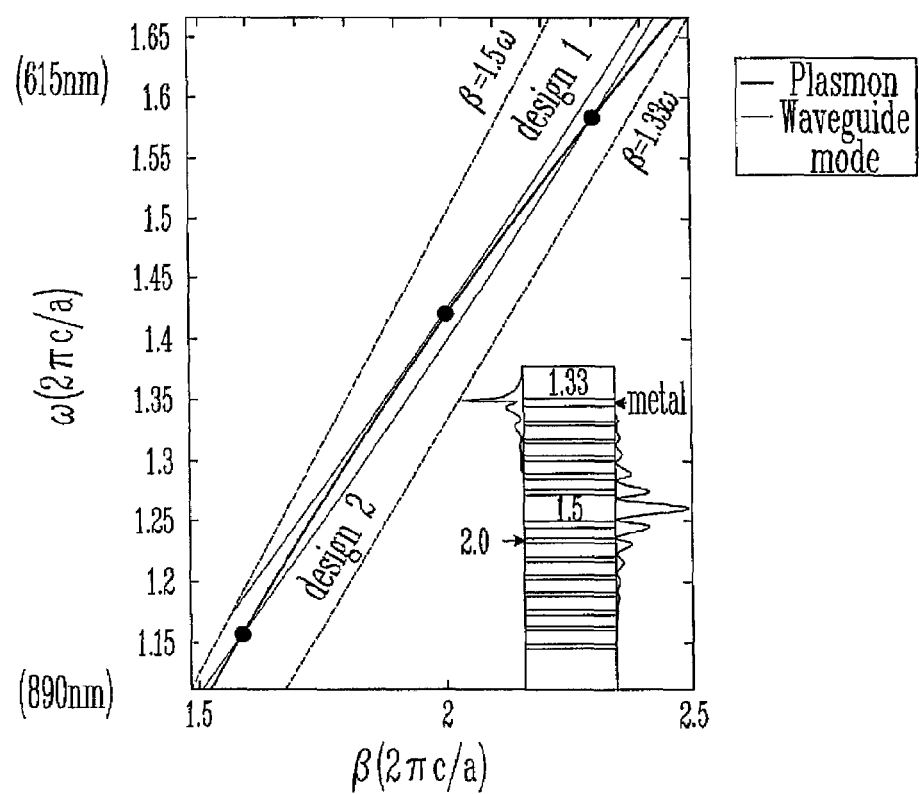
FIG. 1c represents band diagrams of a core mode of a photonic crystal waveguide and plasmon, wherein two waveguide designs (design 1 and design 2) are used for demonstrating that phase matching points can be chosen at will.

In FIG. 1c, two (2) waveguide designs (design 1 and design 2) are used for demonstrating that phase matching points can be chosen at will. In FIG. 1c, the inset is a schematic coupler and the field H of the plasmon and core mode of the photonic crystal waveguide extends along the Y direction. Moreover, in design 1 only a single phase matching point between the core guided mode and the plasmon is featured, with dispersion relation curves being parallel to each other at that point. When the ambient refractive index changes, the plasmon dispersion curve can shift downwards in FIG. 1c resulting, in the case of design 1, in two closely spaced phase matching points with the plasmon. This constitutes a novel mode of operation of a plasmonic sensor not disclosed before. In design 2 there are two phase matching points at which modal and plasmon dispersion relations are not parallel to each other. In the case of design 2, shift of the plasmon dispersion curve due to a change in the ambient refractive index only leads to the change in the positions of the phase matching points.

Since an incoming laser beam (not shown) is Gaussian-like, power coupling efficiency into the sensing mode of core 18 is high due to good spatial mode matching. Moreover, coupling into the sensing mode of core 18 can be further simplified by choosing the thickness (core diameter in the case of a fiber) of core 18 significantly larger than the wavelength of operation in the sensing mode of core 18. This is generally possible as antiguiding waveguides operate in an effective single mode regime regardless of the size of the core 18. Leaky core mode can be easily phase matched with a plasmon mode by design, since the effective refractive index of such a plasmon mode can be readily tuned to be well below the value of the refractive index of the core 18. Another important aspect of the non-restrictive illustrative embodiment is a freedom of adjusting coupling strength between the core and plasmon modes. As field intensity of a leaky mode reduces exponentially into the multilayer reflector 20, coupling strength between the plasmon and waveguide core modes can be controlled or adjusted by changing the number of individual layers of the reflector 20 between the waveguide core 18 and the metal coating or film 16. The smaller is the number of individual layers in the reflector separating the waveguide core 18 and plasmonic layer (metal coating 16), the stronger is the interaction between the waveguide core mode and the plasmon. Interaction strength between the core guided mode and plasmon translates directly into the loss of the core guided mode. Part of this loss is a radiation loss due to the leaky nature of a waveguide core mode, while another part is due to absorption of the modal energy by the metal coating 16. Therefore, loss of the core guided mode is higher for a reflector such as 20 containing a smaller number of individual layers between the waveguide core 18 and a metal coating 16. Finally, the overall length of a sensor is inversely related to the loss of the core guided mode. Therefore, sensor length can be also controlled directly by the number of the individual layers of the reflector such as 20 separating the waveguide core 18 and a metal layer (metal coating 16).

A mode for sensing is excited into the waveguide core 18, the mode for sensing being characterized by an effective refractive index $n_{\mathit{eff}}$. The mode for sensing in the waveguide core 18 is chosen such that the effective refractive index $n_{\mathit{eff}}$ is lower than each of the refractive indices of the individual layers in the photonic crystal 12, not including the substrate 15.

In summary, the following conditions are present:

$n_{\mathit{eff}} < n_{\mathit{core}}$ $n_{\mathit{eff}} < n_{\mathit{analyte}} = 1.332$ (approximate refractive index of water in the visible spectral region);

$n_{\mathit{metal}}$ describes the dispersion relation of gold;

$n_{\mathit{substrate}} = 1.5$ and, in general, is chosen arbitrarily. Experimentally, it can be advantageous to choose $n_{\mathit{eff}} < n_{\mathit{subsate}}$. In this case a core guided Gaussian-like mode is a truly leaky mode and effective single mode operation is possible as higher order (lossier) modes will irradiate into the substrate 15;

$n_{\mathit{high}} = n_{I1} = n_{I3} = n_{I5} = n_{I7} = n_{I9} = n_{I1} = n_{I12} = n_{I14} = n_{I16} = n_{I18} = n_{I20} = n_{I22} = n_{I24} = n_{I26} = 2.0$;

$n_{\mathit{low}} = n_{I2} = n_{I4} = n_{I6} = n_{I8} = n_{I10} = n_{I13} = n_{I15} = n_{I17} = n_{I19} = n_{I21} = n_{I23} = n_{I25} = 1.5$; and $n_{\mathit{eff}} < 1,5$.

With the above conditions, with $n_{\mathit{core}} = n_{\mathit{low}}$ and with a design wavelength $\lambda_d$, an effective refractive index of the fundamental TE and TM modes of a PC waveguide can be designed at will such that $0 \leq n_{\mathit{eff}} < n_{\mathit{low}}$ by choosing the thicknesses of the individual layers I1-I26 and the core 18 such that:

$$d_{low}\sqrt{n_{low}^2 - n_{eff}^2} = d_{high}\sqrt{n_{high}^2 - n_{eff}^2} = \frac{\lambda_d}{4}$$

and $$d_{core} = 2d_{low}$$

wherein $d_{\mathit{low}}$ = thickness of the individual layers with a refractive index of 1.5;

$d_{\mathit{high}}$ = thickness of the individual layers with a refractive index of 2.0; and $d_{\mathit{core}}$ = thickness of core 18.

For this choice of structural parameters, the field distribution in the waveguide core 18 is Gaussian-like both for TE and TM modes whenever $$n_{eff} > \frac{n_{low}n_{high}}{\sqrt{n_{low}^2 + n_{high}^2}}$$

[20], which is, in particular, satisfied for the water analyte with the abovementioned choice of refractive indices. By choosing the effective refractive index $n_{\mathit{eff}}$ of the waveguide core mode to be that of the plasmon, a desired phase matching condition is achieved. For a photonic crystal waveguide with a finite number of individual layers such as I1-I26, design principles hold substantially. Thus, at a wavelength of operation equal to $\lambda = 640$ nm, phase matching is achieved when the photonic crystal 12 is designed with the following parameters:

$n_{\mathit{eff}} = 1.46$; and $\lambda_d = 635$ nm.

Figure 2:
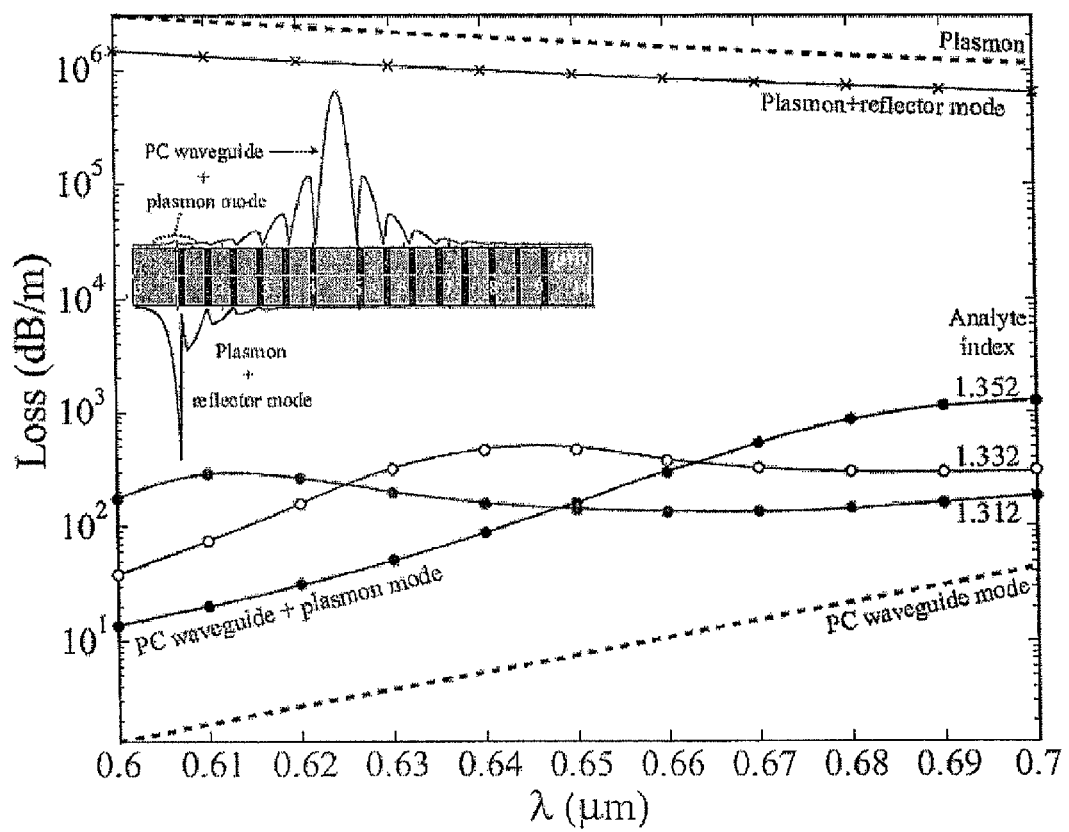
FIG. 2 is a schematic diagram representing a behavior of losses of a core mode of a photonic crystal waveguide-based SPR sensor.

FIG. 2 presents a schematic behavior of losses of a core mode of a photonic crystal waveguide-based SPR sensor. The solid lines with circles represent the loss of a waveguide mode near the phase matching point with a plasmon for different values of the ambient refractive index. Near a phase matching point, fields of a core guided mode contain strong plasmon contribution, as shown on the inset of FIG. 2. As plasmon exhibits very high propagation loss, the loss of a core mode, i.e. the curves with circles of FIG. 2, will also exhibit sharp increase near the phase matching point. For comparison, the dashed line curve at the bottom of FIG. 2 shows the loss of a core guided mode in the absence of coating 16 on top of the photonic crystal 12. When the ambient refractive index changes, the plasmon dispersion relation also changes leading to a shift in the position of the phase matching point with a core guided mode. Thus, at a given frequency, loss of a core guided mode will vary dramatically with changes in the ambient refractive index. Field distribution in a plasmon mode propagating on the top of a photonic crystal 12 shows some penetration into the multilayer structure and losses almost independent of the ambient refractive index, as can be seen on the curve with crosses in FIG. 2. By comparison, the dashed-line curve at the top of FIG. 2 corresponds to the plasmon losses in the absence of multilayer reflector 20.

Figure 3A:
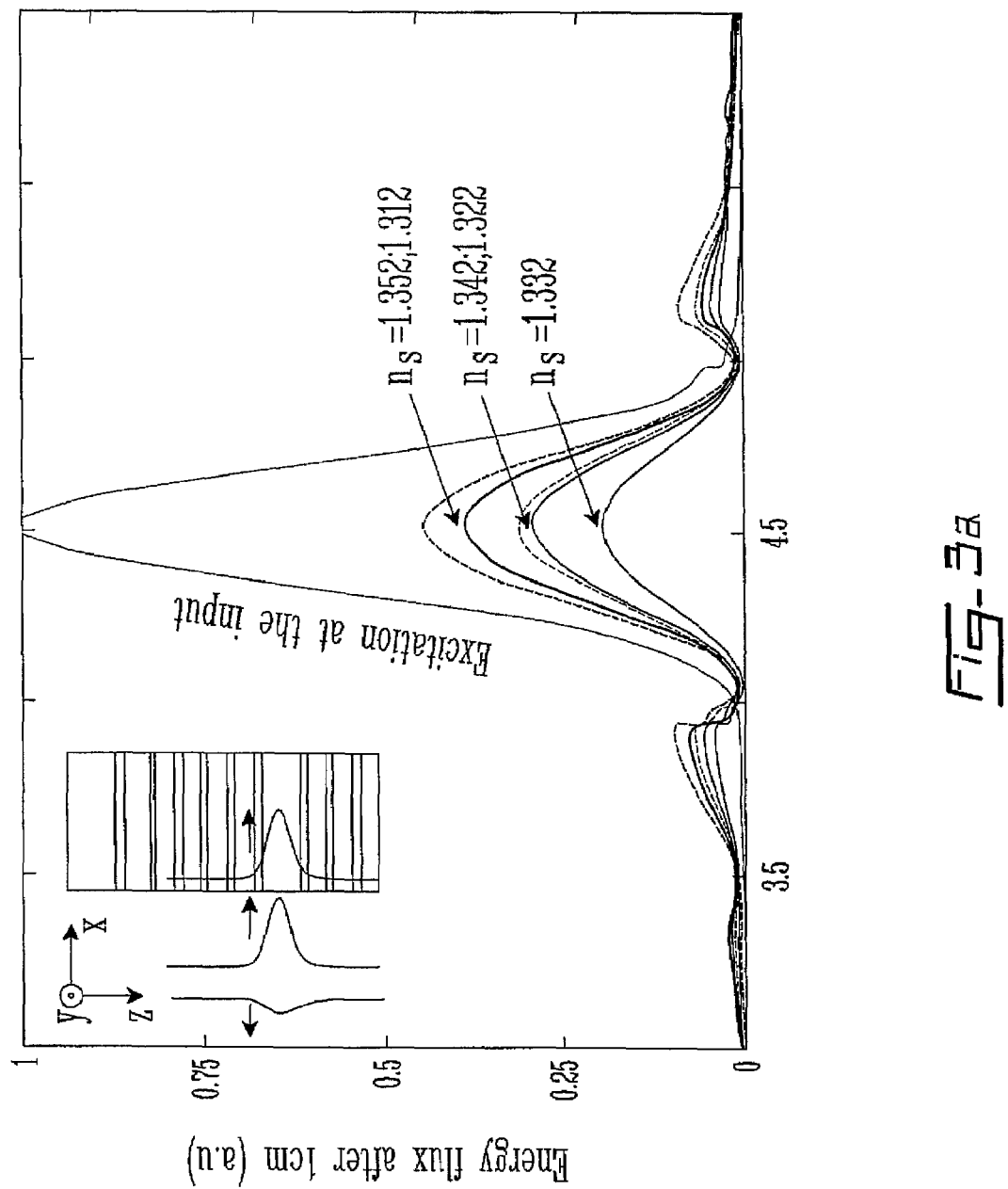
FIGS. 3a and 3b show distributions of energy flux $S_x$ in a multilayer waveguide for various values of ambient refractive indices across the waveguide cross section after 1 cm of propagation (FIG. 3a) and over 2 cm of propagation (FIG. 3b)

Referring now to FIG. 3a, a field propagation was performed. A TM polarized 2D Gaussian beam (H field along a Y direction) was launched into the photonic crystal waveguide-based SPR sensor 10 from air, as illustrated in the inset of FIG. 3a. At the air/multilayer interface, the incoming Gaussian beam was expanded into the fields of all the guided and leaky, and some evanescent multilayer modes (60 altogether), plus the field of a reflected Gaussian beam by imposing continuity of the Z and Y field components at the air/multilayer interface (coupling facet of the sensor 10). Optimal coupling of 71% of an incoming power into the Gaussian-like core mode was achieved with a Gaussian beam of waist $0.8d_c$ centered in the middle of the waveguide core 18. Back reflection from the air/multilayer interface was less than 3%.

Figure 3B:
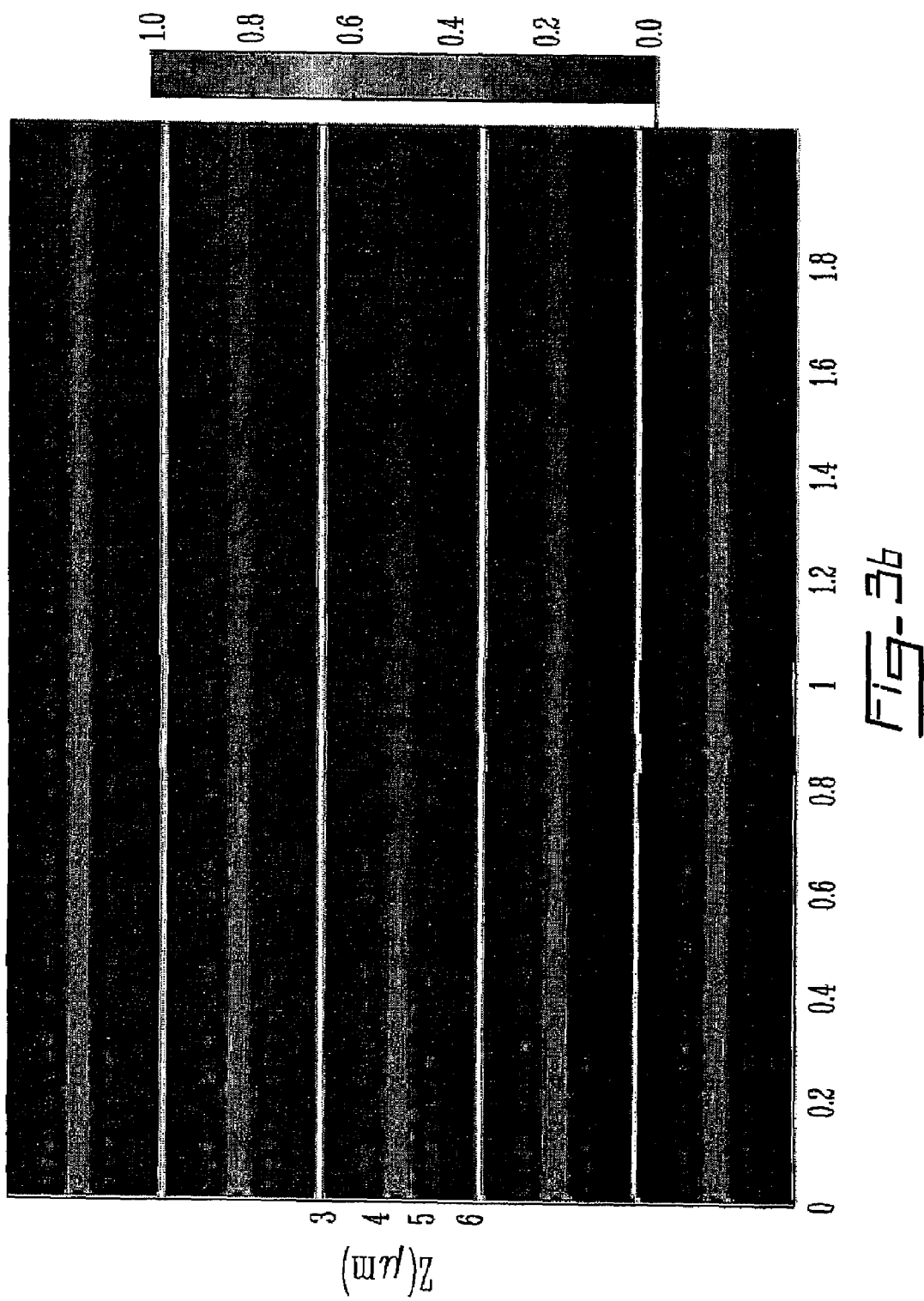

FIG. 3b shows the distribution of an X component (parallel to the waveguide direction) of an energy flux $S_x$ in a propagating beam for various values of an ambient refractive index. From FIG. 3b, it can be seen that the beam propagation loss is very sensitive to changes of the ambient refractive index $n_{\mathit{analyte}}$. To quantify sensitivity of photonic crystal waveguide-based SPR sensor 10, FIG. 3a presents the distribution of energy flux $S_x$ across a cross section of the photonic crystal 12 after 1 cm of beam propagation through the waveguide. From FIG. 3a, it is possible to calculate that a change in the integrated energy flux over the waveguide cross section as a function of the ambient index deviation from the value of 1.332 for pure water can be approximated as:

$$\frac{|\Delta P|}{P_{1.332}} \cong 60|n_{analyte} - 1.332|$$

wherein
P=integrated energy flux over the waveguide crossection which is a quantity actually measured by optical detectors.

Thus, an absolute variation of ~0.0002 in the ambient refractive index leads to approximately a 1% variation in the transmitted power flux which is readily detectable. This constitutes an amplitude-based method for SPR sensing.

An alternative strategy assumes that sensing is performed by detecting the value of a spectral shift $\Delta\lambda$ in the position of the point of maximal loss of the core guided mode (plasmonic peak), with respect to the ambient index deviation from 1.332. In this case, the sensitivity of the photonic crystal waveguide-based SPR sensor 10 will be:

$$|\Delta\lambda| \cong 3500 \text{nm} \cdot |n_{analyte} - 1.332|$$

Thus, an absolute variation of ~0.0003 in the ambient refractive index leads to approximately a 1 nm shift in the position of a plasmonic peak which is readily detectable. This constitutes a spectral method for SPR sensing.

Similar calculations can be carried out assuming that the refractive index of water stays unchanged, while on top of the metal coating 16 a very thin layer of thickness $d_{bio}$ of a biological material with a refractive index of 1.42 is deposited. In this case, sensitivity of the photonic crystal waveguide-based SPR sensor 10 using, for example, amplitude based sensing will be:

$$\frac{|\Delta P|}{P_{1.332}} \cong \frac{0.05 \cdot d_{bio}}{1 \text{ nm}}$$

Thus, deposition of a ~0.2 nm thick bio-layer leads to approximately a 1% variation in the transmitted power which is readily detectable.

Accordingly, adding a bio-layer having thickness of 0.2 nm change the transmitted power by about 1%.

The photonic crystal waveguide-based SPR sensor 10 can also be used in a phase-sensitive configuration. In one implementation of such a scheme a TE polarized mode is used as a reference mode, a TM polarized mode is used as a sensing mode, and light is launched partially both into the TE and TM modes. At the output, the resultant intensity corresponding to the interference between the two modes is detected. Detection of changes in the resulting intensity of the two interfering modes can be used to substantially improve sensitivity of the above suggested sensor.

The configuration of the photonic crystal waveguide-based SPR sensor 10 facilitates plasmon excitation at steeper angles of modal incidence and at lower frequencies, resulting in advantageous sensitivity of beam propagation loss in respect of an ambient refractive index, and enlarged probe depth.

The multilayer reflector 20 surrounding the waveguide core 18 enables an electromagnetic radiation to be confined in the core 18, despite the lower refractive index of this core 18. As a result, the photonic crystal 12 can act as an antiguiding waveguide.

Also, photonic crystals are periodic optical structures of which the design affects the motion of photons in a similar way that periodicity of a semiconductor crystal affects the motion of electrons. More specifically, photonic crystals are composed of periodic dielectric or metallo-dielectric structures that are designed to affect the propagation of electromagnetic waves (EMW) in the same way as the periodic potential in a semiconductor crystal affects the electron motion by defining allowed and forbidden electronic energy bands. The absence of allowed propagating EMW modes inside the structures, in a range of wavelengths called photonic band gap, gives rise to distinct optical phenomena such as inhibition of spontaneous emission, high-reflecting omni-directional mirrors and low-loss waveguiding amongst others.

A plasmon excitation is advantageously induced by submitting the waveguide core 18 to a Gaussian-like transverse-magnetic (TM) polarized laser beam which has the spatial distributions of its vector field components similar to those of the mode in the core of an antiguiding photonic crystal waveguide 12 (see FIGS. 3a and 4). Power coupling efficiency into the core mode is high due to good spatial mode matching. Overall, for a wide range of material refractive indices of reflector materials, the TM polarized core guided mode will have a Gaussian-like (bell like) intensity and energy flux ($S_x$) distribution in the waveguide core layer. Moreover, in some cases, coupling to the photonic crystal 12 can be further simplified by selecting the thickness (core diameter in the case of a fiber) of the waveguide core 18 so as to be significantly larger than the wavelength of the Gaussian-like TM polarized laser beam. This is made possible since anti-guiding waveguides operate in an effective single mode regime regardless of the size of the waveguide core. Finally, excitation of the core guided mode can also be performed with different degrees of success with a generally converging or diverging light beam.

It is to be noted that a leaky core mode can be easily phase-matched with a plasmon mode by design in a wide frequency range from the visible spectral region to near IR (infrared) spectral regions, as the effective refractive index of such a mode can be readily tuned to be well below the value of the waveguide core index. Another aspect of the present invention is a freedom of adjusting coupling strength between the core and plasmonic modes. As penetration of a leaky mode reduces exponentially into the multilayer reflector 20, coupling strength between the plasmon and core modes can be controlled by changing the number of individual reflector layers between the waveguide core 18 and a metal coating or film 16; a smaller number of individual layers in the reflector 20 results in a stronger coupling. Higher coupling strength between the core guided mode and plasmon translates directly into the higher loss of the core guided mode. As the sensor length is generally inversely proportional to the loss of a sensing core mode, it can thus be directly controlled by the number of individual layers of the reflector 20 between the waveguide core 18 and a metal coating 16.

Figure 1D:
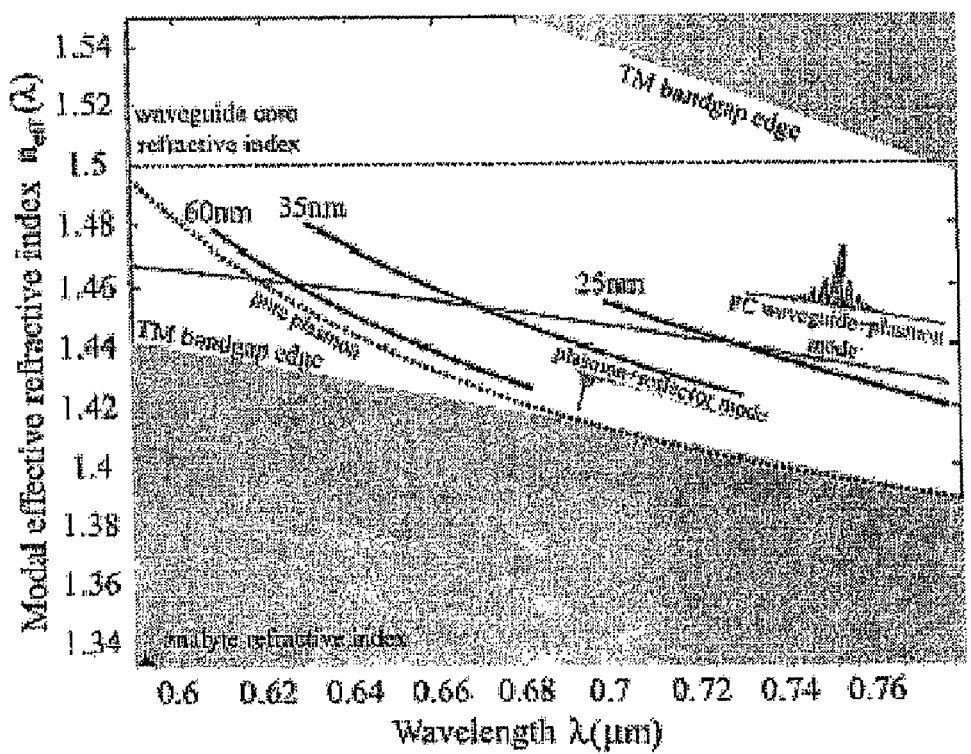
FIG. 1d is a graph showing effective refractive indexes of the modes of a photonic crystal waveguide-based SPR sensor.

FIG. 1d presents effective refractive indexes of the modes of a photonic crystal waveguide-based SPR sensor such as sensor 10 of FIG. 4. Gray regions signify TM polarized bulk states of an infinitely periodic PC reflector. The clear region corresponds to a reflector TM band gap. The thin line, marked as a PC waveguide+plasmon mode, is a dispersion relation of a Gaussian-like core mode of the PC waveguide with most of its energy concentrated in the low refractive index core. The real part of the dispersion relation of the core guided mode is almost insensitive to the metal layer thickness. The thick lines, marked as plasmon+reflector modes, show the dispersion relation of the plasmon modes for various thicknesses of the metallic layer. Here, most of the plasmon modal energy is concentrated on the metal-ambient interface, while some of it is present in the reflector. Due to a partial penetration of the plasmon evanescent wave into the reflector, the plasmon dispersion relation appears to be very sensitive to the thickness of the metallic layer. For comparison, a dotted line shows the dispersion relation of a pure plasmon corresponding to an infinitely thick metal layer. It should be noticed that the coupling between the leaky Gaussian-like core mode and the plasmon is evanescent inside of the reflector band gap with the coupling strength decreasing exponentially as the number of reflector layers increases.

Figure 5:
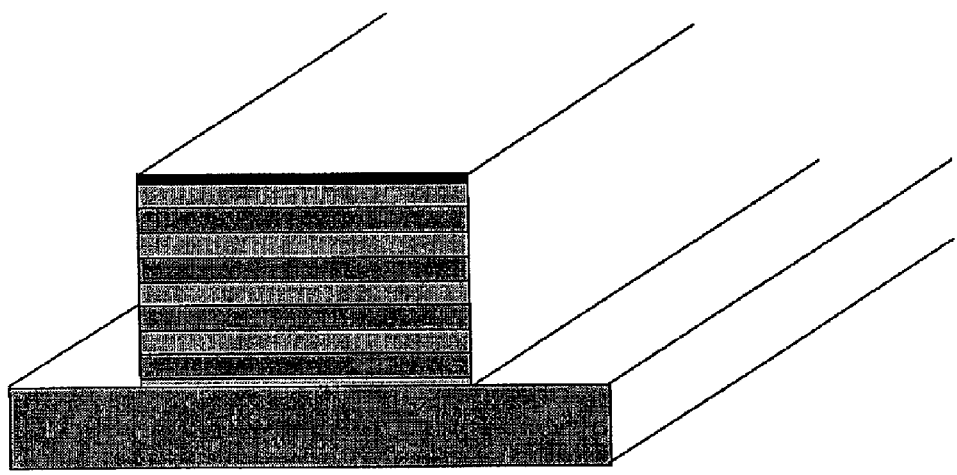
FIG. 5 is a perspective end view of a non-limitative implementation of a multilayer SPR sensor integrated into a planar waveguide, wherein guidance in a transverse direction is ensured by a total internal reflection, whereas guidance in a vertical direction is ensured by multilayer reflection.

It should be noted that the present invention can be implemented with geometries other than that of the non-restrictive illustrative embodiment. For example, FIG. 5 shows a multi-layer SPR sensor integrated with a planar waveguide, wherein guidance in a transverse direction is ensured by the total internal reflection, whereas guidance in a vertical direction is ensured by multilayer reflector.

Figure 6:
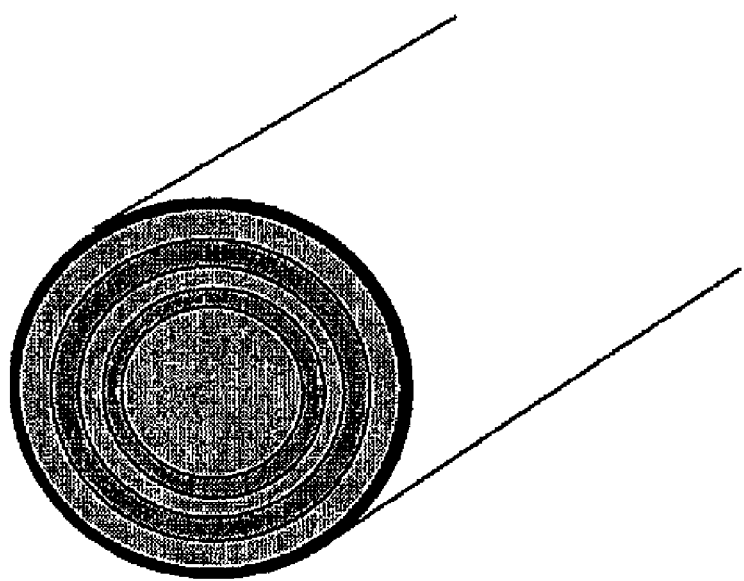
FIG. 6 is a perspective end view of a non-limitative implementation of a multilayer SPR sensor integrated into a Bragg fiber, wherein guidance in a transverse direction is ensured by a band gap of a Bragg fiber cylindrical multilayer reflector.
Figure 7:
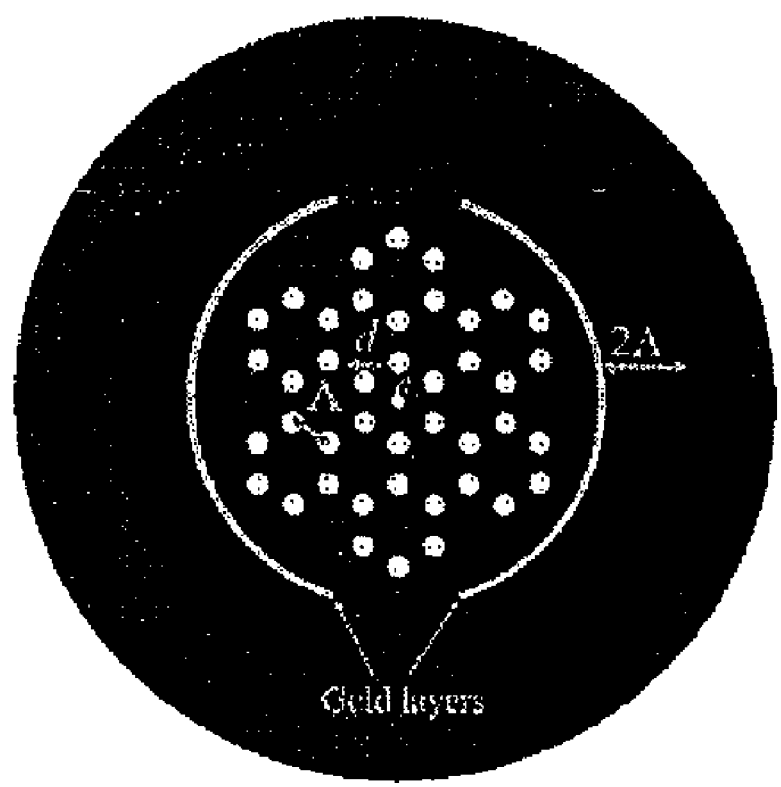
FIG. 7 is an elevation, end view of a non-limitative implementation multilayer SPR sensor integrated into a photonic crystal fiber, wherein guidance in a transverse direction is ensured by a band gap of a photonic crystal fiber reflector.

Circular geometries, such as fiber geometries, are possible for implementing the present invention. Examples of such geometries are shown in FIGS. 6 and 7. FIG. 6 shows a metallized photonic band gap Bragg fiber with a lower index core, which can be used to implement a radial index distribution similar to that of FIG. 1d. Also, microstructured holey fibers, as shown on FIG. 7, operating in a band gap regime with metallized holes on the periphery can be used.

Although the present invention has been described hereinabove by way of a non-restrictive illustrative embodiment thereof, this embodiment can be modified at will, within the scope of the appended claims, without departing from the spirit and nature of the subject invention.

REFERENCES

[1] V. M. Agranovich, D. L. Mills. Surface Polaritons—Electromagnetic Waves at Surfaces and Interfaces, (North-Holland, Amsterdam, 1982).
[2] E. Kretschmann, H. Raether, "Radiative decay of non radiative surface plasmons excited by light," Natur-forschung A 23, 2135 (1968).
[3] Liedberg, C. Nylander, I. Lundstrom, "Surface plasmon resonance for gas detection and biosensing," Sens. Actuators B 4, 299 (1983).
[4] J. L. Melendez, R. Carr, D. U. Bartholomew, K. A. Kukanskis, J. Elkind, S. S. Yee, C. E. Furlong, R. G. Woodbury, "A commercial solution for surface plasmon sensing," Sens. Actuators B 35, 212 (1996).
[5] L. M. Zhang and D. Uttamchandani, "Optical chemical sensing employing surface plasmon resonance," Electron. Lett. 23, 1469 (1988).
[6] A. V. Kabashin and P. Nikitin, "Surface plasmon resonance interferometer for bio- and chemical-sensors," Opt. Commun. 150, 5 (1998).
[7] A. N. Grigorenko, P. Nikitin, and A. V. Kabashin, "Phase jumps and interferometric surface plasmon resonance imaging," Appl. Phys. Lett. 75, 3917 (1999).
[8] P. Schuck, "Use of surface plasmon resonance to probe the equilibrium and dynamic aspects of interactions between biological macromolecules," Annu. Rev. Biophys. Biomol. Struct. 26, 541 (1997).
[9] C. P. Layers, J. S. Wilkinson, "A waveguide-coupled surface-plasmon sensor for an aqueous environment," Sens. Actuators B 22, 75 (1994).
[10] R. Harris and J. S. Wilkinson, "Waveguide surface plasmon resonance sensors," Sens. Actuators B 29, 261 (1995).
[11] M. N. Weiss, R. Srivastava, and H. Grogner, "Experimental investigation of a surface plasmon-based integrated-optic humidity sensor," Electron. Lett. 32, 842 (1996).
[12] J. Homola, J. Ctyroky, M. Skalky, J. Hradiliva, and P. Kolarova, "A surface plasmon resonance based integrated optical sensor," Sens. Actuators B 39, 286 (1997).
[13] J. Dostalek, J. Ctyroky, J. Homola, E. Brynda, M. Skalsky, P. Nekvindova, J. Spirkova, J. Skvor, and J. Schrofel, "Surface plasmon resonance biosensor based on integrated optical waveguide," Sens. Actuators B 76, 8 (2001).
[14] A. K. Sheridan, R. D. Harris, P. N. Bartlett, and J. S. Wilkinson, "Phase interrogation of an integrated optical SPR sensor," Sens. Actuators B 97, 114 (2004).
[15] R. C. Jorgenson and S. S. Yee, "A fiber-optic chemical sensor based on surface plasmon resonance," Sens. Actuators B 12, 213 (1993).
[16] A. Trouillet, C. Ronot-Trioli, C. Veillas, and H. Gagnaire, "Chemical sensing by surface plasmon resonance in a multimode optical fibre," Pure Appl. Opt. 5, 227 (1995).
[17] J. Ctyroky, J. Homola, P. V. Lambeck, S. Musa, H. J. W. M. Hoekstra, R. D. Harris, J. S. Wilkinson, B. Usievich, and N. M. Lyndin "Theory and modelling of optical waveguide sensors utilising surface plasmon resonance," Sens.Actuators B 54, 66 (1999).
[18] M. Weisser, B. Menges, and S. Mittler-Neher, "Refractive index and thickness determination of monolayers by multi mode waveguide coupled surface plasmons," Sens. Actuators B 56, 189 (1999).
[19] B. D. Gupta, and A. K. Sharma, "Sensitivity evaluation of a multi-layered surface plasmon resonance-based fiber optic sensor: a theoretical study," Sens. Actuators B 107, 40 (2005).
[20] M. Skorobogatiy, "Transverse lightguides in microstructured optical fibers," Opt. Lett. 30, 2991 (2005).
[21] H. Shin, M. F. Yanik, S. H. Fan, R. Zia, and M. L. Brongersma, "Omnidirectional resonance in a metal-dielectric-metal geometry," Appl. Phys. Lett. 84, 4421 (2004).
[22] H. Shin and S. H. Fan, "All-angle negative refraction for surface plasmon waves using a metal-dielectric-metal structure," Phys. Rev. Lett. 96, 073907 (2006).
[23] A. Karalis, E. Lidorikis, M. Lbanescu, J. D. Joannopoulos, and M. Soijacic, "Surface-plasmon-assisted guiding of broadband slow and subwavelength light in air," Phus. Rev. Lett. 95, 063901 (2005).
[24] S. G. Johnson, M. Ibanescu, M. Skorobogatiy, O. Weiseberg, T. D. Engeness, M. Soijacic, S. A. Jacobs, J. D. Joannopoulos, and Y. Fink, "Low-Loss Asymptotically Single-Mode Propagation in Large Core OmniGuide Fibers," Opt. Express 9, 748 (2001).

What is claimed is:

1. A surface plasmon resonance sensor for an ambient medium characterized by a refractive index, the surface plasmon resonance sensor comprising:

an antiguiding waveguide comprising: a core characterized by a refractive index; and a reflector surrounding the core, the reflector having an external surface and being characterized by a band gap and a refractive index higher than the refractive index of the core; and a coating deposited on the external surface of the core, the coating defining with the ambient medium a coating/ambient medium interface suitable to support surface plasmons;

wherein, in operation:

the coating is in contact with the ambient medium;

the antiguiding waveguide is supplied with an electromagnetic radiation to (a) propagate a mode for sensing having an effective refractive index lower than the refractive index of the core and higher than the refractive index of the ambient medium and (b) produce surface plasmons at the coating/ambient medium interface;

the mode for sensing is phase-matched with the surface plasmons at a wavelength within the band gap; and a variation of the refractive index of the ambient medium results in a variation of loss of the sensing mode to detect a feature of the ambient medium.

2. A surface plasmon resonance sensor as recited in claim 1, wherein:

the reflector is a multilayer reflector comprising a plurality of individual layers, each individual layer being characterized by a refractive index, the effective refractive index of the mode for sensing being lower than the refractive index of each of the individual layers.

3. A surface plasmon resonance sensor as recited in claim 2, wherein:

the refractive index of each individual layer equals either to a lower refractive index or to a higher refractive index, the lower refractive index being lower than the higher refractive index, and the lower refractive index being higher than or equal to the refractive index of the core.

4. A surface plasmon resonance sensor as recited in claim 3, wherein:

the individual layers and the core are substantially planar;

the core is interposed between a first and a second individual layers;

the first and second layers have both the higher refractive index; and refractive indices of adjacent individual layers alternate from the higher refractive index to the lower refractive index.

5. A surface plasmon resonance sensor as recited in claim 1, wherein the mode for sensing is independent from the size of the core.

6. A surface plasmon resonance sensor as recited in claim 1, wherein the coating comprises a metal film.

7. A surface plasmon resonance sensor as recited in claim 6, wherein the film is made of a metal selected from the group consisting of gold, silver, copper, nickel, titanium, tantalum and chromium.

8. A surface plasmon resonance sensor as recited in claim 1, wherein the coating comprises a semiconductor.

9. A surface plasmon resonance sensor as recited in claim 1, wherein the waveguide comprises an element selected from the group consisting of a photonic crystal, a hollow core Bragg fiber and a gas-filled capillary.

10. A surface plasmon resonance sensor as recited in claim 1, wherein the electromagnetic radiation comprises a laser beam.

11. A surface plasmon resonance sensor as recited in claim 10, wherein the laser beam is Gaussian-like.

12. A surface plasmon resonance sensor as recited in claim 2, wherein a number of individual layers of the multilayer reflector is chosen according to a desired coupling strength between modes of the plasmon and modes of the core.

13. A surface plasmon resonance sensor as recited in claim 1, wherein a thickness of the core is significantly larger than a wavelength of operation.

14. A surface plasmon resonance sensor as recited in claim 1, wherein the mode for sensing comprises a leaky mode having an effective refractive index lower than the refractive index of the core.

15. A surface plasmon resonance sensor as recited in claim 1, wherein, in operation, when the mode for sensing is produced over a sufficient length, the antiguiding waveguide behaves substantially like a single-mode waveguide for any frequency within the band gap, enabling the mode for sensing to phase-match with the surface plasmons at any desirable wavelength within the band gap.

16. A method for surface plasmon resonance sensing a feature of an ambient medium characterized by a refractive index, comprising:

providing an antiguiding waveguide comprising: a core characterized by a refractive index; and a reflector surrounding the core, the reflector having an external surface and being characterized by a band gap and a refractive index higher than the refractive index of the core; and depositing a coating on the external surface of the core, the coating defining with the ambient medium a coating/ambient medium interface suitable to support surface plasmons;

bringing the coating in contact with the ambient medium;

supplying the antiguiding waveguide with an electromagnetic radiation to (a) propagate a mode for sensing having an effective refractive index lower than the refractive index of the core and higher than the refractive index of the ambient medium and (b) produce surface plasmons at coating/ambient medium interface;

phase-matching the mode for sensing with the surface plasmons at a wavelength within the band gap; and sensing a variation of the refractive index of the ambient medium through a variation of loss of the sensing mode to detect a characteristic of the ambient medium.

17. A method for surface plasmon resonance sensing as recited in claim 16, wherein, in operation, when the mode for sensing is produced over a sufficient length, the antiguiding waveguide behaves substantially like a single-mode waveguide for any frequency within the band gap, enabling the mode for sensing to phase-match with the surface plasmons at any desirable wavelength within the band gap.

18. A method for surface plasmon resonance sensing as recited in claim 16, wherein:

the reflector is a multilayer reflector comprising a plurality of individual layers, each individual layer being characterized by a refractive index, the effective refractive index of the mode for sensing being lower than the refractive index of each of the individual layers.

19. A method for surface plasmon resonance sensing as recited in claim 18, wherein:

the refractive index of each individual layer equals either to a lower refractive index or to a higher refractive index, the lower refractive index being lower than the higher refractive index, and the lower refractive index being higher than or equal to the refractive index of the core.

20. A method for surface plasmon resonance sensing as recited in claim 19, wherein:

the individual layers and the core are substantially planar;

the core index is interposed between a first and a second individual layers;

the first and second layers have both the higher refractive index; and refractive indices of adjacent individual layers alternate from the higher refractive index to the lower refractive index.

21. A method for surface plasmon resonance sensing as recited in claim 16, wherein the mode for sensing is independent from the size of the core.

22. A method for surface plasmon resonance sensing as recited in claim 16, wherein the coating comprises a metal film.

23. A method for surface plasmon resonance sensing as recited in claim 16, wherein the coating comprises a semiconductor.

24. A method for surface plasmon resonance sensing as recited in claim 18, comprising choosing a number of individual layers of the multilayer reflector according to a desired coupling strength between modes of the plasmon and modes of the core.

25. A method for surface plasmon resonance sensing as recited in claim 16, comprising making a thickness of the core significantly larger than a wavelength of operation.

26. A method for surface plasmon resonance sensing as recited in claim 16, wherein the mode for sensing comprises a leaky mode having an effective refractive index smaller than the refractive index of the core.

* * * * *